US008685380B2

(12) United States Patent
Ayala

(10) Patent No.: US 8,685,380 B2
(45) Date of Patent: Apr. 1, 2014

(54) DEODORANT SPRAY

(75) Inventor: Nelson Ayala, Lynchburg, VA (US)

(73) Assignee: C.B. Fleet Company, Inc., Lynchburg, VA (US)

( * ) Notice: Subject to any disclaimer, the term of this patent is extended or adjusted under 35 U.S.C. 154(b) by 0 days.

(21) Appl. No.: 13/279,906

(22) Filed: Oct. 24, 2011

(65) Prior Publication Data

US 2012/0100095 A1 Apr. 26, 2012

Related U.S. Application Data

(60) Provisional application No. 61/406,333, filed on Oct. 25, 2010.

(51) Int. Cl.
*A61K 8/00* (2006.01)
*A61L 9/01* (2006.01)

(52) U.S. Cl.
USPC ............... 424/76.8; 424/65; 424/76.1

(58) Field of Classification Search
None
See application file for complete search history.

(56) References Cited

U.S. PATENT DOCUMENTS

| | | | |
|---|---|---|---|
| 4,010,253 A | | 3/1977 | Reese et al. |
| 4,565,693 A | | 1/1986 | Marschner |
| 4,606,912 A | * | 8/1986 | Rudy et al. ............ 424/52 |
| 4,675,177 A | | 6/1987 | Geary |
| 5,643,559 A | | 7/1997 | Eigen et al. |
| 5,770,185 A | | 6/1998 | Wachter et al. |
| 5,968,488 A | | 10/1999 | Wachter et al. |
| 6,277,359 B1 | | 8/2001 | Raths et al. |
| 2004/0033984 A1 | | 2/2004 | Muller |
| 2006/0057090 A1 | * | 3/2006 | Buchwald-Werner ..... 424/70.13 |
| 2007/0281047 A1 | * | 12/2007 | Henry et al. .............. 424/776 |
| 2008/0008727 A1 | | 1/2008 | Fredon et al. |
| 2008/0138850 A1 | * | 6/2008 | Vielhaber et al. ............. 435/29 |
| 2009/0068255 A1 | * | 3/2009 | Yu et al. ................... 424/450 |
| 2009/0220444 A1 | * | 9/2009 | Teckenbrock et al. ......... 424/66 |
| 2012/0083467 A1 | | 4/2012 | Ayala |

FOREIGN PATENT DOCUMENTS

WO 91/07165 5/1991

OTHER PUBLICATIONS

Boonme, P., Songkro, S., Antiperspirants and Deodorants: Active Ingredients and Novel Formulations, Journal of Clinical Dermatology (Review Article), vol. 1, Issue 2, Sep. 23, 2010, pp. 67-72.*
Alvinwriter, Why Choose pH-Balanced Deodorants, Article Alley, (http://alvinwriter.articlealley.com/why-choose-phbalanced-deodorants-573497.html), Jul. 10, 2008.*
McKetta Jr, J.,"Low pH Shampoos" in: Encyclopedia of Chemical Processing and Design (1981), vol. 12, pp. 110-111.*
Sodium Cocol Hydrolyzed Wheat Protein, EWG's Skin Deep® Cosmetics Database, (http://www.ewg.org/skindeep/ingredient/706047/SODIUM_COCOYL_HYDROLYZED_WHEAT_PROTEIN/).*
Zinc Glycinate, EWG's Skin Deep® Cosmetics Database (http://www.ewg.org/skindeep/ingredient/724924/ZINC_GLYCINATE/).*
Sodium Laureth Sulfate, EWG's Skin Deep® Cosmetics Database (http://www.ewg.org/skindeep/ingredient/706089/SODIUM_LAURETH_SULFATE/).*
Polysorbate 20, CosmeticsINFO.org (http://www.cosmeticsinfo.org/ingredient_details.php?ingredient_id=454).*
Parril, A., "Amino Acid Structures", Michigan State University Department of Chemistry, Feb. 4, 1997, <www.cem.msu.edu/~cem252/sp97/ch24/ch24aa.html>, p. 1-2.*
Nordqvist, C., "What is Body Odor (B.O.)? What Causes Body Odor", Medical News Today, Dec. 9, 2009, <www.medicalnewstoday.com/printerfriendlynews.php?newsid=173478>, p. 1-6.*
EWG's Skin Deep® Cosmetics Database, "Queen Helene Deodorant Stick", <http://www.ewg.org/skindeep/product/129714/Queen_Helene_Deodorant_Stick,_Tea_Tree_Oil_(old_formulation)/>, updated Oct. 2009, p. 1-3.*
Neolone Bactericide for Personal Care Products, "Neolone™ MxP Preservative", www.rhpersonalcare.com/neoloneMxP.html, pp. 1-2, printed on Jul. 1, 2009.
Product Description, Neolone™ MXP, www.dow.com/products/market/personal-care-and-apparel/product-line/neolone-for-personal-care/product/neolone-mxp/, 1 page, printed on Jul. 1, 2009.
Product Description and directions, Summer's Eve Feminine Deodorant Spray, Baby Powder, www.drugstore.com/summers-eve-deodorant-spray-baby-powder/qxp214451?catid=184079, 2 pages, printed on Mar. 23, 2009.
Product Description, "Zinc glycinate", Chem Blink, www.chemblink.com/products/14281-83-5.htm, 1 page, printed on Apr. 24, 2009.
Artiaga, F. "Facts on vaginal odor", Livestrong.com, www.livestrong.com/article/2773-facts-vaginal-odor/, pp. 1-3, (2011), printed on Aug. 16, 2012.
Pruthi, S. "Vaginal odor: What causes it?", MayoClinic.com, www.mayoclinic.com/health/vaginal-odor/AN00097, pp. 1-2, (2007), printed on Apr. 22, 2009.
U.S. Appl. No. 13/240,416, Jun. 12, 2013, pp. 14.
U.S. Appl. No. 13/240,416, Mailed Dec. 31, 2013, 18 Pages.

* cited by examiner

*Primary Examiner* — James H Alstrum Acevedo
*Assistant Examiner* — Monica Shin
(74) *Attorney, Agent, or Firm* — Evan Law Group LLC

(57) ABSTRACT

A deodorant comprises triethyl citrate, zinc glycinate, and water. The deodorant has a pH of 5.5 to 6.5.

27 Claims, No Drawings

DEODORANT SPRAY

REFERENCE TO RELATED APPLICATIONS

This application claims the benefit of U.S. Provisional Application No. 61/406,333 entitled "Deodorant Spray" filed Oct. 25, 2010, which is incorporated by reference in its entirety.

BACKGROUND

Vaginal odor is a common problem for women around the world. Many attribute the unpleasant odor to lack of cleanliness. In actuality, the odor is caused by an imbalance in the bacteria within the vagina. Both "good" and "bad" bacteria naturally exist in the vaginal area. However, when the natural ratio of good to bad bacteria becomes imbalanced the result is an unpleasant odor. Vaginal odor can have a significant impact on the lives of those who suffer from it. The sometimes intense odor can adversely impact quality of life by causing those afflicted to shy away from both social and intimate contact. This can significantly affect the ability to construct and maintain healthy relationships.

Triethyl citrate is a compound which can be, and often is, used as the active ingredient in deodorants. It is effective as such because of its ability to inhibit the growth of bacteria associated with the components of sweat. Triethyl citrate is actually consumed by the bacteria in sweat, causing the release of citric acid and ethanol, both of which inhibit the Krebs cycle disrupting the bacterial metabolism. Such inhibition prevents the production of energy by the bacteria and in essence kills the bacteria. Triethyl citrate is slightly water soluble and functions at an optimal pH of 5, therefore when applied directly to the skin this slight acidity is often irritating.

Zinc glycinate is a compound which is also frequently used as an active ingredient in many deodorant products. Zinc glycinate inhibits the growth of the odor causing bacteria found in sweat by obstructing a pathway necessary for the growth of the bacteria. Zinc glycinate is water soluble (about 6 grams per 100 ml cold water) and functions at an optimal pH of range of 7-8. Due to the mildness of the pH, the compound is both safe and effective for use in deodorant products that are applied to, or come in close contact with, the skin.

SUMMARY

In a first aspect, the present invention is a deodorant, comprising triethyl citrate, zinc glycinate, and water. The deodorant has a pH of 5.5 to 6.5.

In a second aspect, the present invention is a deodorant, comprising 0.1 to 10.0% zinc glycinate, 0.1 to 7.0% triethyl citrate, optionally, 0.1 to 10.0% emollient, optionally, 0.1 to 10.0% surfactant, optionally, 0.013 to 1.32% cleansing surfactant, optionally, 0.04 to 4.0% moisturizer, optionally, 0.011 to 1.13% surfactant solubilizer, optionally, 0.05 to 5.0% preservative, optionally, 0.004 to 0.4% fragrance, and water. The deodorant has a pH of 5.5 to 6.5.

In a third aspect, the present invention is a method of making a deodorant, comprising mixing ingredients comprising zinc glycinate, triethyl citrate, and water; and adjusting the pH of the deodorant to 5.5 to 6.5.

All percentage amount described herein are weight/weight percentages (w/w %).

DETAILED DESCRIPTION

While triethyl citrate and zinc glycinate have both been used separately in deodorant products, the combined use of the two ingredients has been avoided due to their differing optimal pH levels. The present invention makes use of the discovery that both triethyl citrate and zinc glycinate are sufficiently effective at a pH range of 5.5-6.5. The combination of these two compounds makes for an effective deodorant spray. However, because of the slightly acidic nature of this combination such a product could be irritating to the skin. The present invention also makes use of the discovery that this deodorant composition is effective to control odor when applied to the clothing, rather than directly to the skin. Because both main compounds are strongly drawn to both hair and fabric, the active ingredients in the product remain adhered to the clothing long after the initial application; upon application, the clothing itself is in essence made anti-bacterial, controlling any odor caused by bacteria. Also, because the present invention may be formulated as a clear solution, there is no worry about staining clothing. The present invention provides strong, lasting, deodorant protection.

A spray deodorant composition contains anti-bacterial agents used to reduce the amount of bacteria found on the skin and/or hair, when the composition is applied to clothing in contact with the skin and/or hair. The composition uses a combination of zinc glycinate and triethyl citrate as anti-bacterial agents. Both triethyl citrate and zinc glycinate are sufficiently effective at a pH range of 5.5-6.5. Preferably, zinc glycinate is present in an amount of 0.1 to 10%, more preferably 0.2 to 8%, and most preferably 0.5 to 5%, including 0.6, 0.7, 0.8, 0.9, 1, 1.5, 2, 2.5, 3, 3.5, 4 and 4.5%. Preferably, triethyl citrate is present in an amount of 0.1 to about 7% (the solubility limit in water), more preferably 0.2 to 6%, and most preferably 0.5 to 3.5%, including 0.6, 0.7, 0.8, 0.9, 1, 1.5, 2, 2.5 and 3%.

Preferably, the composition is supplied in a spray bottle, so that it may be sprayed onto clothing, particularly undergarments such as underwear or panties. The composition could also be applied as a spray to a feminine napkin, menstrual pad or other clothing in contact with the pubic area. The resulting fabric, paper or cloth, will contain the composition, and provide the deodorant effect.

The pH of the composition is maintained in the range of 5.5-6.5, including 5.6, 5.7, 5.8, 5.9, 6.0, 6.1, 6.2, 6.3 and 6.4. The composition may optionally include a pH modifier used to obtain the desired pH level. Some examples of pH modifiers are phosphoric acid (for example 75% w/w), hydrochloric acid, and trifluoroacetic acid.

The composition may optionally contain an emollient used to sooth the skin. Examples of emollients include propylene glycol, propylene glycol esters (for example propylene glycol laurate, propylene glycol myristate, and propylene glycol linoleate) and dimethicones (for example dimethicone PEG-8 beeswax, dimethicone PEG-7 isostearate, and dimethicone PEG-8 phosphate). Preferably, the emollient is present in an amount of 0.1 to 10%, more preferably 0.2 to 8%, and most preferably 0.5 to 5%, including 0.6, 0.7, 0.8, 0.9, 1, 1.5, 2, 2.5, 3, 3.5, 4 and 4.5%.

The composition may optionally contain a surfactant used to reduce the surface tension of the composition to a range of between below 35-40 dynes per centimeter, therefore allowing the invention to be used as a spray. Examples of surfactants are polysorbates (for example, polysorbate 20, polysorbate 21, polysorbate 40 and polysorbate 80 acetate), polyglyceryls (for example, polyglyceryl-2 tetrastearate, polyglyceryl-6 undecylenate, polyglyceryl-10 trioleate) and butylenes glycols (for example butylene glycol behenate, butylene glycol laurate and butylene glycol oleate). Preferably the surfactant is present in an amount of 0.1 to 10%, more preferably 0.2 to 8%, and most preferably 0.5 to 5%, including 0.6, 0.7, 0.8, 0.9, 1, 1.5, 2, 2.5, 3, 3.5, 4 and 4.5%.

The composition may optionally contain a cleansing surfactant. Some examples of cleansing surfactants include cocoamphocarboxyglycinate, laureths (laureth-16, laureth-7 phosphate and laureth-4 carboxylic acid) and myristamidopropyls (myristamidopropyl betaine, myristamidopropyl hydroxysultaine and myristamidopropyl dimethylamine phosphate). Preferably the cleansing surfactant is present in an amount of 0.013 to 1.32%, more preferably 0.025 to 1.0%, and most preferably 0.065 to 0.65, including 0.07, 0.08, 0.09, 0.1, 0.12, 0.15, 0.2, 0.3, 0.4 and 0.5%.

The composition may optionally contain a moisturizer. Examples of moisturizers include PEGylated lanolins (for example, PEG-75 lanolin), PEGylated fatty acid esters (for example PEG-6 glyceryl tristearate, PEG-4 glyceryl tristearate, and PEG-25 glyceryl trioleate) and PEGylated oils. Preferably the moisturizer is present in an amount of 0.04 to 4%, more preferably 0.08 to 2%, most preferably 0.1 to 1%, including 0.2, 0.25, 0.3, 0.35, 0.4, 0.5, 0.6, 0.7, 0.8 and 0.9%.

The composition may optionally contain a surfactant solubilizer, which may also aid in cleansing. An example of a surfactant solubilizer is cocamidopropylamine oxide. Preferably the surfactant solubilizer is present in an amount of 0.011 to 1.13%, more preferably 0.02 to 0.95%, most preferably 0.055 to 0.225%, including 0.06, 0.07, 0.08, 0.09, 0.1, 0.15 and 0.2%.

The composition may optionally contain a preservative. Example preservatives include the parabens, such as methylparaben, ethylparaben, propylparaben, butylparaben, and their salts. Other preservatives include phenoxyethanol, methylisothiazoline, benzoic acid, 1,3-bis(hydroxymethyl)-5,5-dimethylimidazolidine-2,4-dione (also known as DMDM hydantoin), and sodium hydroxymethyl glycinate. Preferred preservatives include commercially available preservative blends, for example the NEOLONE™ family of preservatives (available from Rohm & Haas, Philadelphia, Pa.), such as NEOLONE™ MXP (a mixture including phenoxyethanol, methylparaben, propylparaben and methylisothiazolone). Preferably the preservative is present in an amount of 0.05 to 5%, more preferably 0.1 to 4%, and most preferably 0.2 to 2.5%, including 0.25, 0.3, 0.35, 0.4, 0.45, 0.5, 0.6, 0.7, 0.8, 0.9, 1.0, 1.5 and 2.0%.

The composition may optionally include fragrances. Preferably, fragrances may be present in an amount of 0.004 to 0.4%, more preferably 0.01 to 0.2%, most preferably 0.02 to 0.1%, including 0.025, 0.03, 0.035, 0.04, 0.045, 0.05, 0.06, 0.07, 0.08 and 0.09%. Purified water is added to balance.

Once the composition is applied to clothing, paper or fabric, the water may evaporate, leaving the component in the proportions described above, although not necessarily in the specified weight percentages.

EXAMPLE

An example formulation is as follows:

| | |
|---|---|
| Propylene glycol | 1.000 |
| Polysorbate 20 | 1.000 |
| Zinc glycinate | 1.000 |
| Triethyl citrate | 1.000 |
| PEG-75 lanolin | 0.400 |
| Cocoamphocarboxyglycinate | 0.132 |
| Cocamidopropylamine oxide | 0.113 |
| Neolone MXP | 0.500 |
| Fragrance | 0.040 |
| Phosphoric acid 75% w/w | 0.015 |
| Purified water | Remainder |

Target pH = 5.5-6.5

What is claimed is:

1. A deodorant, comprising:
triethyl citrate,
zinc glycinate,
cocamidopropylamine oxide, and
water,
wherein the deodorant has a pH of 5.5 to 6.5.

2. The deodorant of claim 1, further comprising an emollient.

3. The deodorant of claim 2, wherein the emollient is selected from the group consisting of propylene glycol, propylene glycol esters, dimethicones and mixtures thereof.

4. The deodorant of claim 1, further comprising a surfactant.

5. The deodorant of claim 4, wherein the surfactant is selected from the group consisting of polysorbates, polyglyceryls, butylenes glycols and mixtures thereof.

6. The deodorant of claim 1, further comprising a cleansing surfactant.

7. The deodorant of claim 6, wherein the cleansing surfactant is selected from the group consisting of cocoamphocarboxyglycinate, laureths, myristamidopropyls and mixtures thereof.

8. The deodorant of claim 1, further comprising a moisturizer.

9. The deodorant of claim 8, wherein the moisturizer is selected from the group consisting of PEGylated lanolins, PEGylated fatty acid esters, PEGylated oils and mixtures thereof.

10. The deodorant of claim 1, further comprising a preservative.

11. The deodorant of claim 10, wherein the preservative is selected from the group consisting of the parabens, phenoxyethanol, methylisothiazoline, benzoic acid, 1,3-bis(hydroxymethyl)-5,5-dimethylimidazolidine-2,4-dione, sodium hydroxymethyl glycinate and mixtures thereof.

12. The deodorant of claim 1, further comprising a fragrance.

13. A deodorant, comprising:
0.1 to 10.0% zinc glycinate,
0.1 to 7.0% triethyl citrate,
optionally, 0.1 to 10.0% emollient,
optionally, 0.1 to 10.0% surfactant,
optionally, 0.013 to 1.32% cleansing surfactant,
optionally, 0.04 to 4.0% moisturizer,
0.011 to 1.13% cocamidopropylamine oxide,
optionally, 0.05 to 5.0% preservative,
optionally, 0.004 to 0.4% fragrance, and
water,
wherein the deodorant has a pH of 5.5 to 6.5.

14. The deodorant of claim 13, wherein the zinc glycinate is present in an amount of 0.5 to 5%.

15. The deodorant of claim 13, wherein the triethyl citrate is present in an amount of 0.5 to 3.5%.

16. A method of making the deodorant of claim 1, comprising:
mixing ingredients comprising:
the zinc glycinate,
the triethyl citrate,
the cocamidopropylamine oxide, and
the water; and
adjusting the pH of the deodorant to 5.5 to 6.5.

17. A deodorant, prepared by a method comprising:
mixing ingredients comprising:
zinc glycinate,
triethyl citrate,
cocamidopropylamine oxide, and
water; and
adjusting the pH of the deodorant to 5.5 to 6.5.

18. The deodorant of claim 13, comprising the emollient in an amount of 0.5 to 5.0%.

19. The deodorant of claim 13, comprising the surfactant in an amount of 0.5 to 5.0%.

20. The deodorant of claim 13, comprising the cleansing surfactant in an amount of 0.065 to 0.65%.

21. The deodorant of claim 13, comprising the moisturizer in an amount of 0.1 to 1.0%.

22. The deodorant of claim 13, comprising the cocamidopropylamine oxide in an amount of 0.055 to 0.225%.

23. The deodorant of claim 13, comprising the preservative in an amount of 0.2 to 2.5%.

24. The deodorant of claim 13, comprising the fragrance in an amount of 0.02 to 0.1%.

25. The deodorant of claim 13, comprising:
0.1 to 10.0% zinc glycinate,
0.1 to 7.0% triethyl citrate,
0.1 to 10.0% emollient,
0.1 to 10.0% surfactant,
0.013 to 1.32% cleansing surfactant,
0.04 to 4.0% moisturizer,
0.011 to 1.13% cocamidopropylamine oxide,
0.05 to 5.0% preservative,
0.004 to 0.4% fragrance, and
water,
wherein the deodorant has a pH of 5.5 to 6.5.

26. The deodorant of claim 13, comprising:
0.2 to 8.0% zinc glycinate,
0.2 to 6.0% triethyl citrate,
0.2 to 8.0% emollient,
0.2 to 8.0% surfactant,
0.025 to 1.0% cleansing surfactant,
0.08 to 2.0% moisturizer,
0.02 to 0.95% cocamidopropylamine oxide,
0.1 to 4.0% preservative,
0.01 to 0.2% fragrance, and
water,
wherein the deodorant has a pH of 5.5 to 6.5.

27. The deodorant of claim 13, comprising:
0.5 to 5.0% zinc glycinate,
0.5 to 3.5% triethyl citrate,
0.5 to 5.0% emollient,
0.5 to 5.0% surfactant,
0.065 to 0.65% cleansing surfactant,
0.01 to 1.0% moisturizer,
0.055 to 0.225% cocamidopropylamine oxide,
0.2 to 2.5% preservative,
0.02 to 0.1% fragrance, and
water,
wherein the deodorant has a pH of 5.5 to 6.5.

* * * * *

UNITED STATES PATENT AND TRADEMARK OFFICE
CERTIFICATE OF CORRECTION

PATENT NO. : 8,685,380 B2  
APPLICATION NO. : 13/279906  
DATED : April 1, 2014  
INVENTOR(S) : Nelson Ayala It is certified that error appears in the above-identified patent and that said Letters Patent is hereby corrected as shown below:

On the Title Page:

(73) Assignee:
Please delete "C.B. Fleet Company, Inc." and insert --C. B. Fleet Company Incorporated--.

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,685,380 B2
APPLICATION NO. : 13/279906
DATED : April 1, 2014
INVENTOR(S) : Nelson Ayala Page 1 of 1

It is certified that error appears in the above-identified patent and that said Letters Patent is hereby corrected as shown below:

On the Title Page, Item (56) References Cited

Col. 2, Line 47, after "13/240,416," insert --Mailed--
Col. 2, Line 47, delete "pp. 14." and insert --14 Pages.--

In the Claims

Col. 4, line 38, delete "the" prior to parabens

Signed and Sealed this
First Day of September, 2015

Michelle K. Lee
*Director of the United States Patent and Trademark Office*